United States Patent [19]

Ruoslahti

[11] Patent Number: 5,180,808
[45] Date of Patent: Jan. 19, 1993

[54] VERSICAN CORE PROTEIN, NUCLEIC ACID SEQUENCES ENCODING THE SAME, NUCLEIC ACID PROBES, ANTI-VERSICAN ANTIBODIES, AND METHODS OF DETECTING THE SAME

[75] Inventor: Erkki I. Ruoslahti, Rancho Santa Fe, Calif.

[73] Assignee: La Jolla Cancer Research Foundation, La Jolla, Calif.

[21] Appl. No.: 441,179

[22] Filed: Nov. 27, 1989

[51] Int. Cl.$^5$ .......................... C07K 3/00; C07H 15/12
[52] U.S. Cl. .................... 530/350; 530/387.9; 530/388.2; 530/389.1; 536/23.5
[58] Field of Search .................. 436/561, 23, 503, 519; 536/27; 530/350, 387

[56] References Cited

PUBLICATIONS

Zimmermann et al. EMBO 8(10), 1989, pp. 2975-2982; abstract only.
Perides et al., Isolation and Partial Characterization of a Glial Hyaluronate-binding Protein, The Journal of Biological Chemistry, 264:5981-5987 (1989).
Saunders et al., Molecular Cloning of Syndecan, an Integral Membrane Proteoglycan, The Journal of Cell Biology 108:1547-1556 (1989).
Stamenkovic et al., A Lymphocyte Molecule Implicated in Lymph Node Homing is a Member of the Cartilage Link Protein Family, Cell 156:1057-1062 (1989).
Oldberg et al., The Primary Structure of a Cell-binding Bone Sialoprotein, The Journal of Biological Chemistry 263:19430-19432 (1988).
Halberg et al., A Segment of the Cartilage Proteoglycan Core Protein Has Lectin-like Activity, The Journal of Biological Chemistry 263:9486-9490 (1988).
Appella et al., Structure and Function of Epidermal Growth Factor-like Regions in Proteins, FEBS Letters 231:1-4 (1988).
Erkki Ruoslahti, Structure and Biology of Proteoglycans, Ann. Rev. Cell Biol. 4:229-55 (1988).
Doege et al., Complete Primary Structure of the Rat Cartilage Proteoglycan Core Protein Deduced from cDNA Clones, The Journal of Biological Chemistry 262:17757-17767 (1987).
Krusius et al., A Fibroblast Chondroitin Sulfate Proteoglycan Core Protein Contains Lecint-Like and Growth Factor-like Sequences, The Journal of Biological Chemistry 262:13120-13125 (1987).
Kiss et al., Structure of the Chicken Link Protein Gene: Exons Correlate with the protein domains, Proc. Natl. Acad. Sci. USA 84:6399-6403 (1987).
Kimata et al, A Large Chondroitin Sulfate Proteoglycan (PG-M) Synthesized before Chondrogenesis in the Limb Bud of Chick Embryo, The Journal of Biological Chemistry 261:13517-13525 (1986).
Yamagata et al., Chondroitin Sulfate Proteoglycan (PG-M-like Proteoglycan) Is Involved in the Binding of Hyaluronic Acid to Cellular Fibronectin, The Journal of Biological Chemistry 261:13526-13535 (1986).
Sai et al, Cloning and sequence analysis of a partial cDNA for chicken cartilage proteoglycan core protein, Proc. Natl. Acad. Sci. USA 83:5081-5085 (1986).
Deak et al., Complete amino acid sequence of chicken cartilage link protein deduced from cDNA clones, Proc. Natl. Acad. Sci. USA 83:3766-3770 (1986).
Johansson et al., Structure and interactions of proteoglycans in the extracellular matrix produced by cultured human fibroblasts, Biochem. J. 232:161-168 (1985).

*Primary Examiner*—Moskowitz: Margaret
*Assistant Examiner*—Bradley L. Sisson
*Attorney, Agent, or Firm*—Campbell and Flores

[57] ABSTRACT

The invention relates to the fibroblast proteoglycan, versican. The versican core protein has the amino acid sequence, and is encoded by the nucleotide sequence, as shown in FIG. 1. The nucleotide sequence and method of hyaluronic acid binding domain is provided and methods of preparing recombinant proteins having hyaluronic acid binding activity are provided. Such protein can be used to determine the presence of hyaluronic acid and as a vehicle to bring other molecules in contact with hyaluronic acid. The complete versican sequence will allow the production of the entire versican molecule to be used, for example, in tissue reconstruction. Nucleic acid probes are provided which are useful for detecting nucleic acid sequences encoding versican. The invention also provides antibodies reactive with versican.

7 Claims, 10 Drawing Sheets

```
                                                                                              86
GCTGCCCGAGCCTTTCTGGGGAAGAACTCCAGGCGTGCGGACGCAACAGCCGAGAACATTAGTGTTGTGGACAGGAGCTGGGAC

266
CAAGATCTTCGGCCAGCCCCGCATCTCCCGCATCTTCCCAGCACCGTCCCGCACCTCCGCATCTTCCCGGGCCACCGCTTCCTA

TGTGACCCGCTGGGCAACGCCGAACCCAGTCGCGCAGCGCTGCAGTGAATTTTCCCCCAAACTGCAATAAGCCGCTTCCAAGGCCAAG

ATGTTCATAAATATAAAGAGACATCTTATGGATGTTCAACCTTAATAGTAACCATGGCTACATAAAGTCAAAGTGGGAAAAAGCCC   446
 M  F  I  N  I  K  S  I  L  W  M  C  S  T  L  I  V  T  H  A  L  H  K  V  K  V  G  K  S  P   60

ACCGGTGAGGGGCTCCCTCTGAAAAGTCAGCCTACTTGTCATTTTCAACGATGCCTACTTTGCCACCCAGTTACAACACCAGTGAA
 P  V  R  G  S  L  S  G  K  V  S  L  P  C  H  F  S  T  M  P  T  L  P  P  S  Y  N  T  S  E

TTTCTCCGCATCAAATGGTCTAAGATTGAAGTGGACAAAAATGGAAAAGATTGAAAGACTACTGTCTTGTGGCCCAAATGGAAA    626
 F  L  R  I  K  W  S  K  I  E  V  D  K  N  G  K  D  L  K  E  T  T  V  L  V  A  Q  N  G  N   120

TATCAAGATTGGTCAGGACTACAAAGGGAGAGTGTCTGTGCCCACACATCCGAGGCTGTGGGGGATGCCTCCCTCACTGTGGTCAAGCTG
 I  K  I  G  Q  D  Y  K  G  R  V  S  V  P  T  H  P  E  A  V  G  D  A  S  L  T  V  V  K  L

CTGGCAAGTGATGCGGGGCTCTTTGCTGCGGCAACCAGCAGGTACACGCTGTGACGTCATGTACGGTACAGGTGTCACTGACTGTGGGGT   806
 L  A  S  D  A  G  L  F  A  A  T  S  R  Y  T  L  N  F  E  A  A  Q  K  A  C  L  D  V  G  V   180

TGTGTTCACTGACAGCAGCTCTTGCTGCCTATGAAGATGGATTTGAGCAGTGTGACGCAGGCTGGCTGATCAGATCCCAT
 V  F  H  Y  R  A  A  T  S  R  Y  T  L  N  F  E  A  A  Q  K  A  C  L  D  V  G  A  V  I  A

ACTCCAGAGCAGCTCTTTGCTGCCTATGAAGATGGATTTGAGCAGTGTGACGCAGGCTGGCTGGCTGATCAGACTGTCAGATATCCCAT
 T  P  E  Q  L  F  A  A  Y  E  D  G  F  E  Q  C  D  A  G  W  L  A  D  Q  T  V  R  Y  P  I

CCGGGCTCCCAGATAGGCTGTGTTAGGGAGTAAGATGGGAAAGGCAGGAGTCAGGAGTTATGGATTCCGTTCTCCCAGGAAACTTACGAT   986
 R  A  P  R  V  G  C  Y  G  D  K  M  G  K  A  G  V  R  T  Y  G  F  F  R  S  P  Q  E  T  Y  D   240

GTGTATTGTTATGTGGATCATCTGGATGGTGATGTGTTCCACCTTACCGTTCCAGTAAATTCACCTTCGAAGGCTGCAAAAGAGTG
 V  Y  C  Y  V  D  H  L  D  G  D  V  F  H  L  T  V  P  S  K  F  T  F  E  E  A  A  K  E  C

TGAAAACCAGGATGCCAGGCTGGCAACAGTGGGGGAACTCCAGGCGGCATGGAGGAACGGCTTTGACCAGTGCGATTACGGGTGCGTGCG   1166
 E  N  Q  D  A  R  L  A  T  V  G  E  L  Q  A  A  W  R  N  G  F  D  Q  C  D  Y  G  W  L  S    300
```

```
CCAGGACCTGATCGCTGCAAAATGAACCCTGCCTTAAGGAGGCACCTGTTATCCTACTGAAACTTCCTAGCTATGCACCTGTGTGCC       6746
 P  G  P  D  R  C  K  M  N  P  C  L  N  G  G  T  C  Y  P  T  E  T  S  Y  V  C  T  C  V  P      2160

AGGATACAGGCGGAGACCAGTGTGACTTGATTTTGATGAATGTCACTCTGTCGTAATGGAGCCACTTGTGTGTGATGGTTTTAAC        6926
 G  Y  S  G  D  Q  C  E  L  D  F  D  E  C  H  S  N  P  C  R  N  G  A  T  C  V  D  G  F  N     2220

ACAATTCAGGTGCCTCTGCCTTCCAAGTTATGTTGGTGCACTTGTGAGCAAGATACCGAGACATGGACTGACTGTGACACAAATTCCA     7106
 T  F  R  C  L  C  L  P  S  Y  V  G  A  L  C  E  Q  D  T  E  T  C  D  Y  G  W  H  K  F  Q     2280

AGGGCAGTGCTACAAATATACTTGCCCATCGACGCAGCACATGGGAATGCAGTCTGCAGGGTGCCCATCTCACAAGCATC             7286
 G  Q  C  Y  K  Y  F  A  H  R  R  T  W  D  A  A  E  R  E  C  R  L  Q  G  A  H  L  T  S  I     2340

CTGTCTCAGAAGACAAATGTTTGTTAATCGTGTGGGGCCATGATTATCAGTGGATAGGCCTCAATGACAAGATGTTTGAGCATGACTT    7466
 L  S  H  E  E  Q  M  F  V  N  R  V  G  H  D  Y  Q  W  I  G  L  N  D  K  M  F  E  H  D  F     2400

CCGTTGGACTGATGGCCAGCAGACACTGGAGAATTGGAGACCAGCAGCTTCTTTTCTGTGGAGAAGACAGTGTGTTGTA              7646
 R  W  T  D  G  S  T  L  Q  Y  E  N  W  R  P  N  Q  P  P  D  S  F  F  S  A  G  E  D  C  V     2409

ATCATTTGGACTGAGAATGGCCAGTGGAATGATGTTCCCTGCAATTACCATCTCACTGCAAGAAAGGAACAGTTGCTTGCGG
 I  W  H  E  N  G  Q  W  N  D  " P  C  N  Y  H  L  T  Y  T  C  K  K  G  T  V  A  C  G

CCAGCCCCCTGTGTAGAAAATGCCAAGACCTTTGGAAAGATGAAACCTCGTTATGAAATCAACTCCCTGATTAGATACCACTGCAAAGAT
 Q  P  P  V  V  E  N  A  K  T  F  G  K  M  K  P  R  Y  E  I  N  S  L  I  R  Y  H  C  K  D

GGTTTCATTCAACGTCACCTTCCAACTTTCCGGTGTGCTTAGGATGTGCATGAACCATCTGC
 G  F  I  Q  R  H  L  P  T  I  R  C  L  G  N  G  R  W  A  I  P  K  I  T  C  M  N  P  S  A

ATACCAAAGGACTTATTCTATGAAATACTTTAAAAATTCCTCATCAGCAAAGGACAATTCCAAACATCAATAAATACATCCAAAGTCCTAACTTCCTGTGC
 Y  Q  R  T  Y  S  M  K  Y  F  K  N  S  S  A  K  D  N  S  I  N  T  S  K  H  D  H  R  W

AGCCGGAGGTGGCAGGAGTCGAGGCGCTGATCCCTAAAAATGGCGAACATGTGTTTCATCATTTCAGCCAAAGTCCTAACTTCCTGTGC
 S  R  R  W  Q  E  S  R  R

CTTTCCTATCACCTCGAGAAGTAATTATCAGTTGGTTTGGATTTTTGGACCACCGTTCAGTCATTTGGGTTGCCGTGCTCCCAAAACATT

FIG. IG
```

```
TTAAATGAAAGTATTGGCATTCAAAAAGACAGCAGACAAAATGAGAGCAGAAAGTAAGCATTCCAGCCTATCTAATTTC
TTTAGTTTCTATTTGCCTCCAGTGCAGTCCATTCCTAATGTATACCAGCCTACTGTACTATTTAAAATGCTCAATTTCAGCACCGATG   7826
GCCATGTAAATAAGATGATTTAATGTTGATTTTAATCCTGTATATAAAATAAAAAGTCACAATGAGTTTGGGCATATTTAATGATGATTA
TGGAGCCTTAGAGGTCTTTAATCATTGGCTGCTGTTTATGTAGTTTAGGCTGGAAATGGTTTCACTTGCTCTTTGACTGTCAGCAA     8006
GACTGAAGATGGCTTTTCCTGGACAGCTAGAAAACACAAAATCTTGTAGGTCATTGCACCTATCTCAGCCATAGGTGCAGTTTGCTTCTA
CATGATGCTAAAGGCTGCGAATGGATCCTGATGGAACTAAGGACTCCAATGTCGAACTCTTCTTTGCTGCATTCCTTTCTTTCTTCACTTA   8186
CAAGAAAGGCCTGAATGGAGGACTTTTCTGTAACCAGG     8224
```

VERSICAN CORE PROTEIN, NUCLEIC ACID SEQUENCES ENCODING THE SAME, NUCLEIC ACID PROBES, ANTI-VERSICAN ANTIBODIES, AND METHODS OF DETECTING THE SAME

This invention relates generally to the field of proteoglycans and more specifically to a large fibroblast proteoglycan.

BACKGROUND OF THE INVENTION

Proteoglycans are a diverse group of proteins that carry a sulfated carbohydrate component, glycosaminoglycan, attached to a core protein. There are four main types of glycosaminoglycan: heparin/heparan sulfate, chondroitin sulfate/dermatan sulfate, keratan sulfate and hyaluronic acid. The core proteins of proteoglycans vary in size from 1,000 to more than 200,000 daltons and the number of glycosaminoglycan chains attached to the core varies from one to about 100. In addition, some proteoglycans also contain N-linked and O-linked oligosaccharides.

Proteoglycans are functionally as well as structurally heterogeneous. Currently, their known or proposed functions include a space-filling or structural role in tissues or at tissue boundaries, regulation of receptor function, regulation of growth and differentiation, regulation of proteinase activities and modulation of cell adhesion.

Large aggregating proteoglycans that carry primarily chondroitin sulfate side chains are present in the extracellular matrix of a wide variety of tissues including cartilage, skin, tendon and placenta. It is likely that these large proteoglycans play a role in cell-extracellular matrix interactions, since their core proteins bind to hyaluronic acid and contain potential binding sites for other molecules.

Some core proteins of proteoglycans contain domains with homologies to various binding elements. For example, the growth-factor-like domains may function in the transmission of regulatory signals to cells and lectin-like domains may bind to oligosaccharides of interstitial collagens. Moreover, one identified proteoglycan domain binds to hyaluronic acid.

Hyaluronic acid is a carbohydrate composed of a repeated sequence of glucuronic acid and Nacetylglucosamine units. Hyaluronic acid appears to play a role in the migration of cells through tissues, such as occurs in development and wound healing. Its presence attracts water, thereby causing swelling of the matrix. It is used as both a tissue substitute and lubricant in wound healing and treatment of joint diseases Because of the importance of proteoglycans in cell function and metabolism, there is a need for additional proteoglycans, particularly those which can interact with hyaluronic acid. The present invention satisfies this need, and provides related advantages as well.

SUMMARY OF THE INVENTION

Figure 1E:
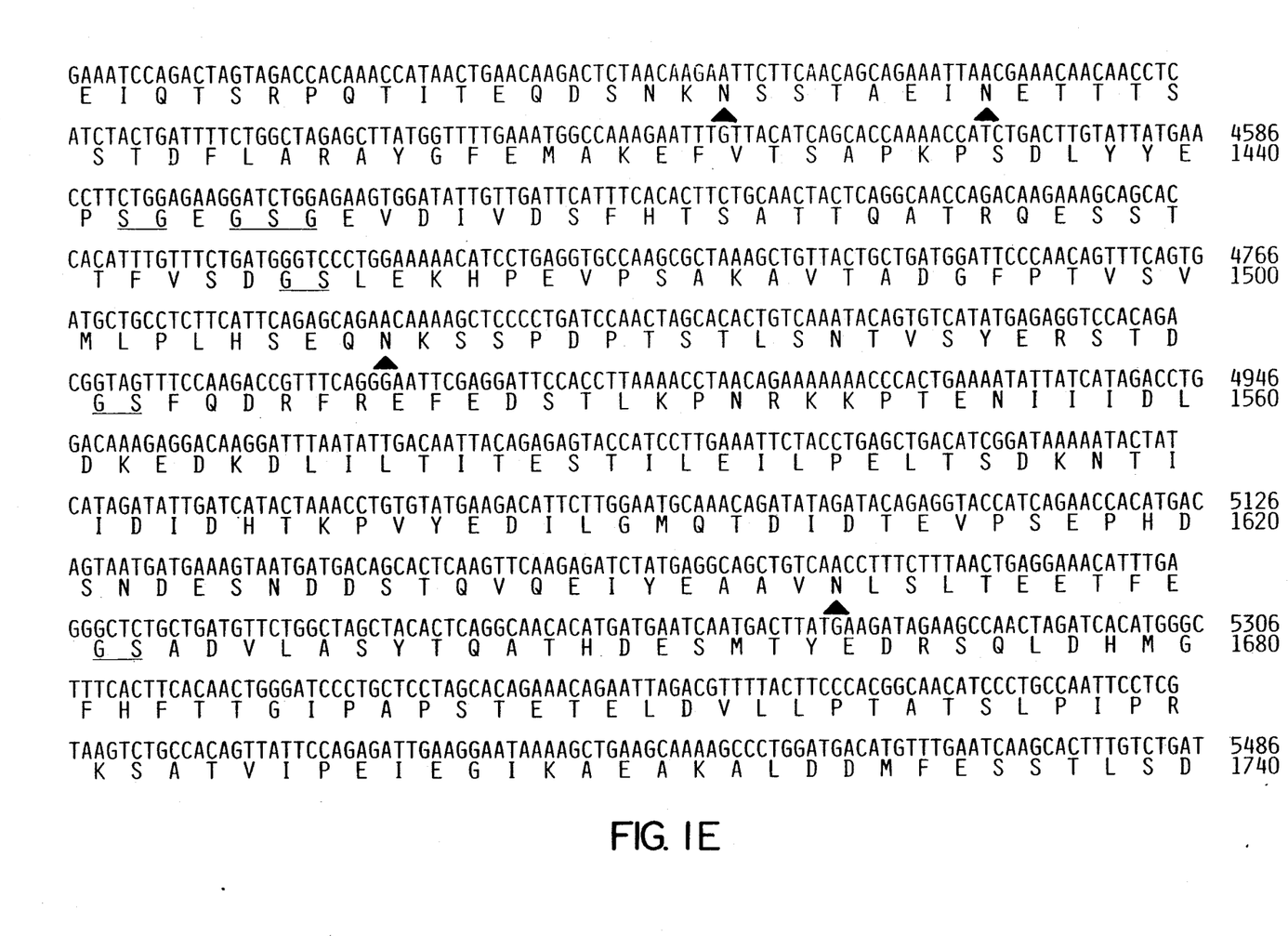
FIG. 1 represents the cDNA and amino acid sequences of versican core protein. The arrow indicates the putative signal cleavage site, dots mark cysteine residues and triangles show potential N-glycosylation sites. Serine in position 371 can be substituted by threonine.
Figure 1G:
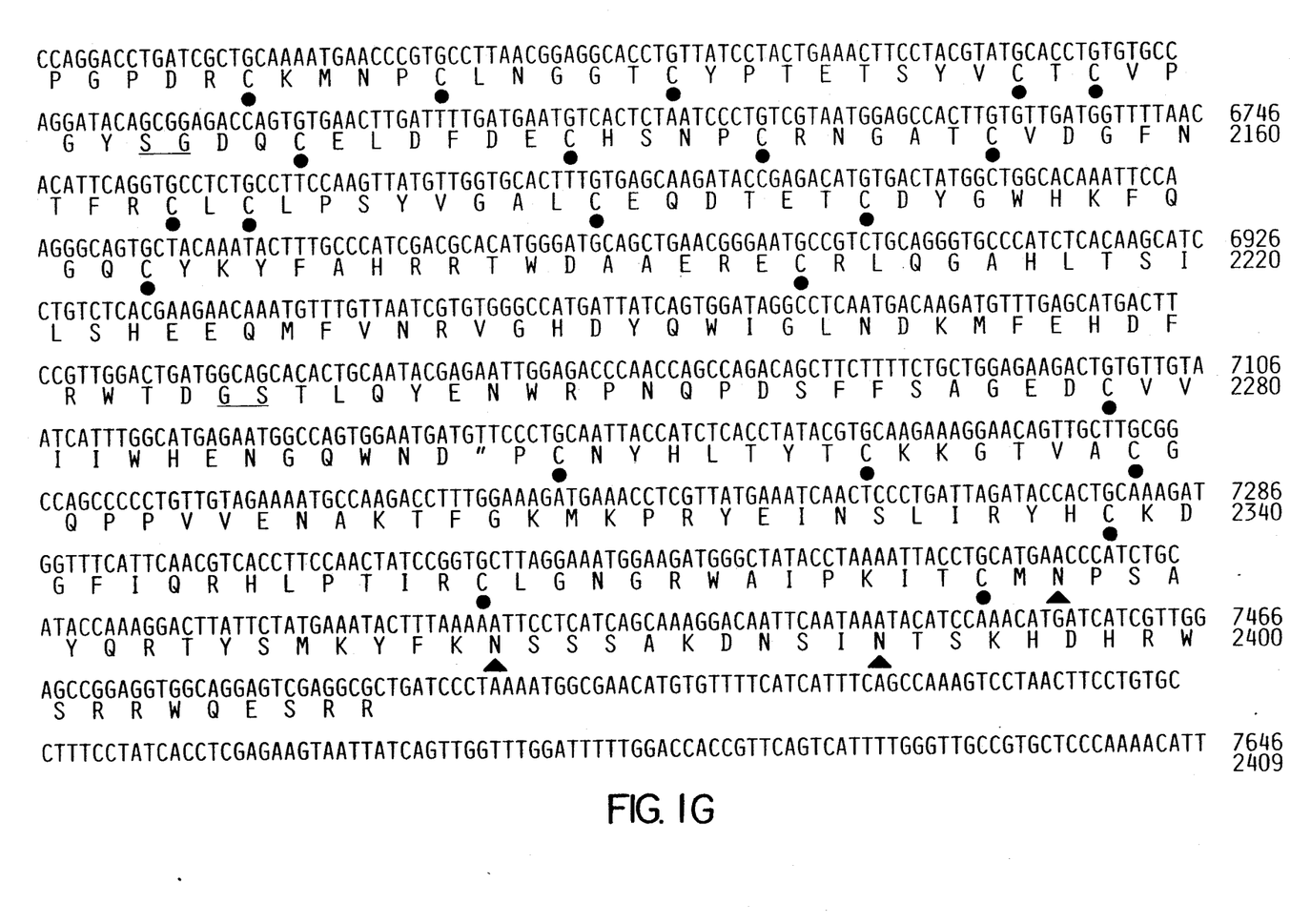
Figure 1H:
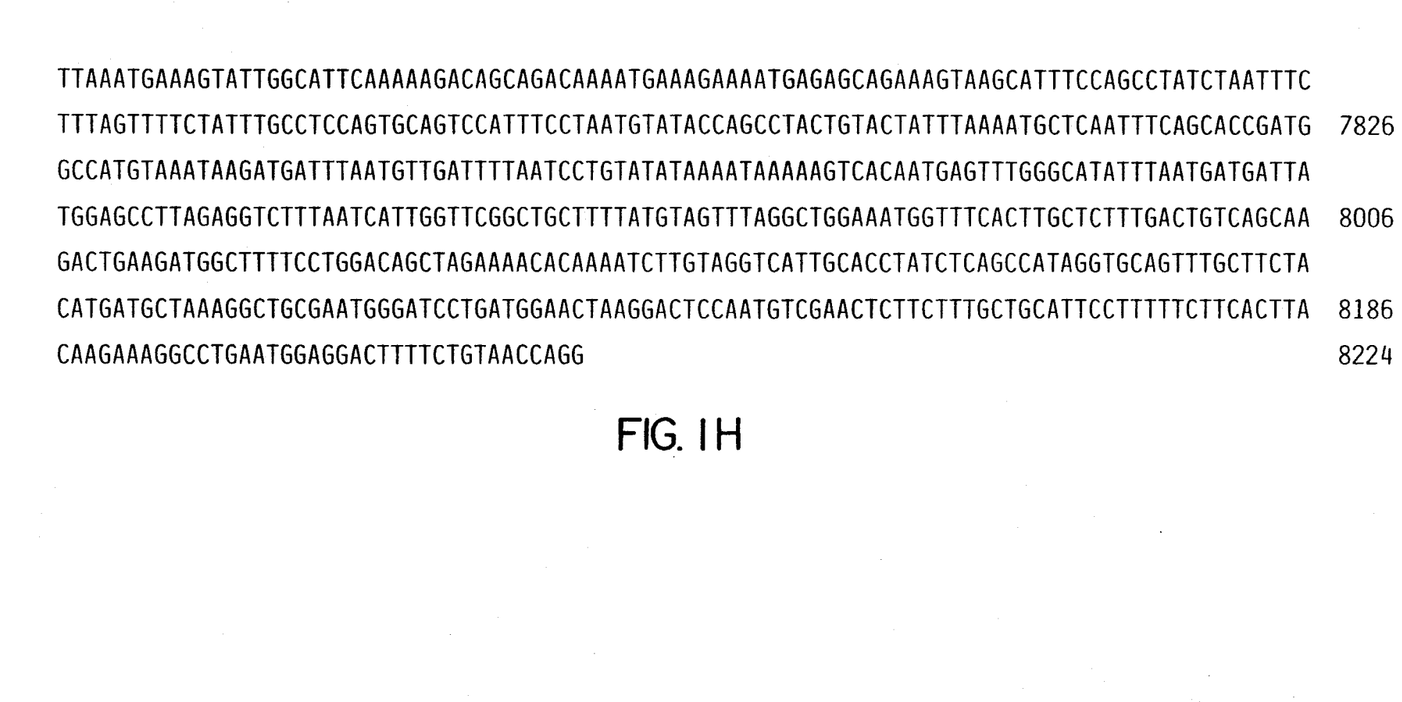

The invention relates to the fibroblast proteoglycan, versican. The versican core protein has the amino acid sequence, and is encoded by the nucleotide sequence, as shown in FIG. 1. The nucleotide sequence encoding the hyaluronic acid binding domain is provided and methods of preparing recombinant proteins having hyaluronic acid binding activity are provided. Such proteins can be used to determine the presence of hyaluronic acid and as a vehicle to bring other molecules in contact with hyaluronic acid. The complete versican sequence will allow the production of the entire versican molecule to be used, for example, in tissue reconstruction. Nucleic acid probes are provided which are useful for detecting nucleic acid sequences encoding versican. The invention also provides antibodies reactive with versican.

DETAILED DESCRIPTION OF THE INVENTION

Versican is a large fibroblast proteoglycan that may play a role in cellular interactions. While previous work has revealed the main structural features of certain proteoglycan core proteins, definitive structural information on versican core protein has only now been obtained through molecular cloning. Versican exhibits unexpected structural differences from other proteoglycan core proteins. Such an unexpected result is that the $NH_2$-terminal domain of versican which contains all the partial amino acid sequences assigned to a hyaluronic acid binding protein called glial hyaluronic acid binding protein.

Using antiserum made against peptides the sequences of which were deduced from versican cDNA clones, versican has been identified as belonging to the chondroitin sulfate proteoglycans. These cDNA clones represented only partial sequences of versican, and therefore additional clones were required, and subsequently identified. The invention provides the complete nucleotide sequence containing a transcription initiation site open reading frame and polyadenylation signal for versican. Given the sequence, a skilled artisan can achieve expression of versican as a product of recombinant DNA, using methods known to those skilled in the art. See generally, Maniatis, MOLECULAR CLONING, Cold Spring Harbor, which is incorporated herein by reference.

Figure 2:
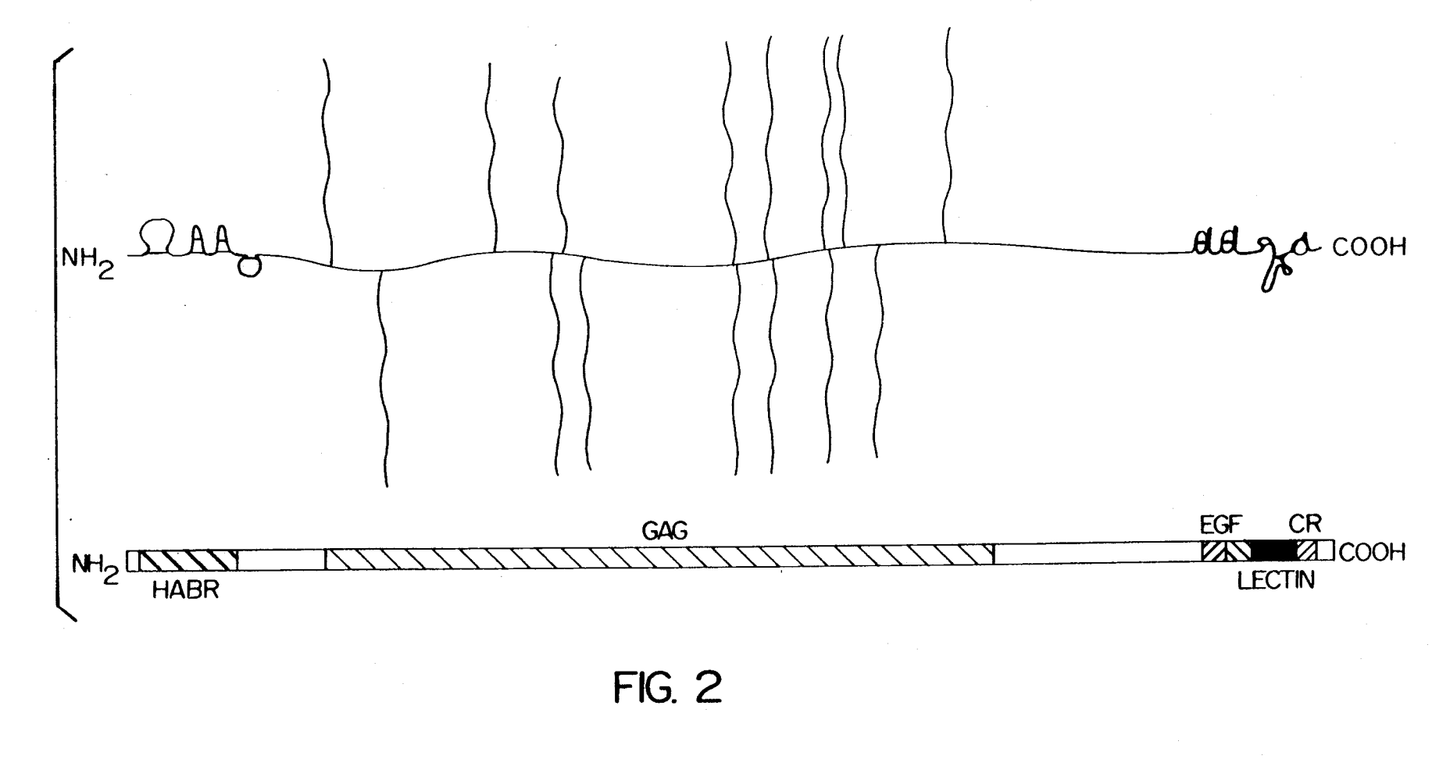
FIG. 2 provides a structural model of versican. The thicker line represents the core protein and wavy lines illustrate chondroitin sulfate side chains. The disulfide bonds were assigned based on structures of similar proteins. The organization of the link protein-like hyaluronic acid binding region (HABR) and glycosaminoglycan attachment (GAG), EGF-like (EGF), lectin-like (lectin) and complement regulatory protein-like (CR) domains of versican are shown schematically.

Versican cDNA clones were isolated by screening a human placental library using radiolabeled fragments of previously identified clones. Overlapping clones covered the entire coding sequence for versican as well as several hundred 5' and 3' flanking base pairs. DNA sequence analysis of the clones revealed a signal peptide, amino terminal hyaluronic acid-binding domain and carboxyterminal EGF-like repeats, lectin-like sequence and complement regulatory protein-like domain. The amino and carboxy-terminal portions of the fibroblast core protein are related to the core protein of the major aggregating chondroitin sulfate proteoglycan of chondrosarcoma cells and cartilage. However, the versican sequence reveals a mosaic structure which is different from that of the cartilage/chondrosarcoma proteoglycan. A structural model for this proteoglycan in which the core protein contains seven distinct domains is shown in FIG. 2. Among these domains are four potential binding elements that may be involved in interactions among extracellular matrix molecules and between cells and extracellular matrices. The amino terminal link protein-like sequence end and the carboxy-terminal EGF-like, lectin-like and complement regulatory protein-like domains have been mentioned above. The intervening 1750-amino acid stretch includes the glycosaminoglycan attachment domain.

The deduced 2409-residue versican, including signal sequence, has a molecular weight of 265,048 daltons. The $NH_2$-terminal 20 amino acids form a typical secretory signal sequence with a putative cleavage site between $Ala_{20}$ and $Leu_2$, in agreement with the (-3, -1) rule. The sequence immediately upstream of the ATG start codon conforms with the consensus sequence for translation initiation in eukaryotes.

The versican core protein is rich in glutamic acid, serine and threonine residues. It is highly negatively charged with a calculated pI of 4.2. There are a total of 34 cysteine residues in the mature protein located exclusively in the amino- and carboxy-terminal domains. Cysteine is absent over a stretch of almost 1700 amino acid residues in the middle of the core protein. The versican core protein contains 20 potential N-glycosylation sites, and a series of serine/threonine clusters (2 sites with 3 and more consecutive Ser/Thr residues) which may serve as acceptors for 0-linked carbohydrates.

On the carboxy-terminal side of the link protein-like sequence is an about 200-amino acid domain containing two cysteines and an unusual cluster of glutamic acid residues (EENEEEEEE). This region is followed by the glycosaminoglycan attachment domain.

The region between amino acid residues 559 and 1654 contains 12 repeats of a series of serine-glycine or glycine-serine sequences. These sequences are likely to carry the glycosaminoglycan chains, attached to serine residues. The consensus sequence of these repeats is E/DGSGE/D, in which one amino acid residue (usually one of the glycines) is variable. This consensus sequence is similar to the attachment site of the single chondroitin sulfate chain in collagen type IX (Huber et al., J. Biol. Chem. 263:752-756 (1988)). Three sequences in the chondroitin/heparan sulfate proteoglycan syndecan (Saunders et al., J. Cell Biol. 108:1547-1556 (1989)) also follow this pattern. Another two sites of versican are similar to the SGXG glycosaminoglycan attachment signal previously established in a group of small proteoglycans (Bourdon et al., Proc. Nat. Acad. Sci. USA 84:3194-3198 (1987)). The glycosaminoglycan side chains might be crucial for maintaining an extended structure that would ensure the separation of the specific functional elements located at the ends of the polypeptide. Such a structure has been established for the cartilage proteoglycan by electron microscopy (Paulsson et al., Biochem. J. 245:763-772 (1987)). Versican contains sixteen additional serineglycine or glycineserine sequences. However, they show little similarity with known chondroitin sulfate attachment sites. Finally, 16 serine/threonine clusters and 10 potential N-glycosylation sites are located in this domain. The sequences of the acids acidic regions and the glycosaminoglycan attachment domain are quite different from any sequences in the large aggregating cartilage proteoglycan. These sequences are, therefore, valuable in providing nucleic acid probes suitable for specific detection of versican mRNA. Moreover, these sequences when translated to protein can provide synthetic peptides and recombinant protein fragments that can be used to prepare antibodies specific for versican.

The globular domain at the $NH_2$-terminus of versican (residues 36 to 348) is similar to the three loop structure of link protein and to the link protein-like sequences in the large cartilage proteoglycan (Deak et al., Proc. Natl. Acad. Sci. USA 83:3766-3770 (1986); Doege et al., Proc. Natl. Acad. Sci. USA 83:3761-3765 (1986); Kiss et al., Proc. Natl. Acad. Sci. USA 84:6399-6403 (1987); Doege et al., J. Biol. Chem. 262:17757-17767 (1987), which are incorporated herein by reference). The amino acid sequences of the B and B' loops, which are known to mediate the hyaluronic acid binding of link protein, are especially well conserved. Moreover, $CDw44/gp90^{Hermes}$, which is thought to be involved in lymphocyte homing, contains a link protein B-loop domain with 30% amino acid sequence identity to versican (Goldstein et al., Cell 56:1063-1072 (1989); Stamenkovic et al., Cell 56:1057-1062 (1989), which are incorporated herein by reference). However, versican contains only one link protein-like domain, whereas the cartilage proteoglycan includes a second partial link protein-like domain. However, electron microscopical data have demonstrated that this second domain is not involved in the interactions of the large cartilage proteoglycan with hyaluronic acid and link protein (Mörgelin et al., Biochem. J. 253:175-185 (1988)).

While the link protein-like domains of the proteins discussed above are only related to the corresponding versican domain, one published link protein-like sequence may be identical to it. Short peptide sequences have been recently reported for a glial hyaluronate-binding protein (GHAP) isolated from human brain white matter (Perides et al., J. Biol. Chem. 264:5981-5987 (1989)). These sequences are virtually identical with sequences within the aminoterminal domain of versican. The few differences probably reflect deamidation reactions and/or sequencing errors. These similarities suggest that GHAP is a proteolytically processed form of versican and that it includes the link protein-like portion and the adjacent glutamic acid rich structure of versican. This was an unexpected finding because GHAP has been thought to be an independent distinct protein. The hyaluronic acid binding proteins, the cartilage proteoglycan and link protein, bind cooperatively to hyaluronic acid. Clearly, the link protein is not needed for the versican $NH_2$-terminal domain to bind to hyaluronic acid since GHAP binds to hyaluronic acid. The DNA sequence provided here, therefore, allows the synthesis of a protein that can bind to hyaluronic acid without the assistance of another protein.

The hyaluronic binding region can be used to determine the presence or amount of hyaluronic acid using an assay analogous to an immunoassay. Many such assay systems and formats are known to those skilled in the art. See ANTIBODIES; A LABORATORY MANUAL (Harlow and Lane, eds.) Cold Spring Harbor Laboratory (1988), which is incorporated herein by reference. For purposes of generating a reagent for assays, the hyaluronic acid binding region or hyaluronic acid can be conjugated with a detectable label, such as, for example, a radioisotope, a component of an enzyme activated system or a chemiluminescent system.

Any immunoassay-type assay format can be used, substituting the hyaluronic acid region for one or more of the antibodies. In one embodiment, the hyaluronic acid in a sample is allowed to complex with the hyaluronic binding region by incubating the sample suspected of containing the hyaluronic acid with the hyaluronic acid binding region. Labelled hyaluronic acid is added to the sample. After the incubation period, the hyaluronic acid complex is separated from the free hyaluronic acid by binding the complex to a solid phase. The solid phase is washed and the complex bound to it is measured. The labeled hyaluronic acid and the hyaluronic acid in the sample will compete for binding to the hyaluronic acid binding region and the uptake of labeled hyaluronic acid is inversely correlated to the amount of antigen in the test solution.

The hyaluronic acid binding domain can also be used to detect the presence of hyaluronic acid in immunohistochemistry. The domain is labeled with a fluorescent reagent, such as fluorescein isothiocyanate, and used in a similar manner in fluorescent antibodies to stain tissue sections, as is well known in the art.

The following examples are intended to illustrate but not limit the invention.

EXAMPLE I

Construction of the random primed cDNA library

Poly-A RNA was isolated from human placenta by the guanidine isothiocyanate method and subsequent chromatography on oligo(dT) cellulose according to the method of Davis et al., 1986, which is incorporated herein by reference. 10 μg of mRNA was primed with 0.5 μg random hexanucleotides (Pharmacia). cDNA synthesis was carried out by using the Amersham cDNA synthesis system. Prior to the first strand synthesis, mRNA and primer were heated for 1 minute at 70°C. and immediately chilled on ice. Reverse transcription was done at 25° C. for 45 min. followed by incubation at 42° C. for 1 hour. The second strand was synthesized by the RNase H / DNA polymerase I procedure of Gubler and Hoffman, Gene 25:263-269 (1983) which is incorporated herein by reference. Internal EcoRI sites were protected by methylation with EcoRI methylase according to the method of Davis et al., BASIC METHODS IN MOLECULAR BIOLOGY, Elsevier, Amsterdam (1986) which is incorporated herein by reference). Phosphorylated EcoRI linkers (decamer, Pharmacia) were blunt-end ligated to the cDNA. The cDNA was restricted with EcoRI and size-fractionated on Sephacryl S-1000 and fragments larger than 0.5 kb, were ligated to EcoRI-restricted and dephosphorylated lambda gt11 arms (Promega). The ligated DNA was packaged with phage extracts (Gigapack Gold, Stratagene Cloning Systems, San Diego, Calif.). The resulting library contained $9 \times 10^6$ recombinants.

Plaque screening and subcloning

The unamplified cDNA library was screened with radiolabeled 5'-fragments (random oligolabeling kit, Boehringer) of the previously characterized clones. DNA of positive clones was isolated, cut with EcoRI and subcloned into pBluescript (KS(+) (Stratagene). Recombinant plasmids were purified by alkaline lysis (Davis et al., Suora) and CsCl gradient centrifugation.

cDNA sequencing

The DNA sequence was determined by the dideoxynucleotide chain termination method by using Sequenase sequencing kit (United States Biochemical Corporation) with Bluescript T3 and T7 primers (Stratagene) or specific 17-mer oligonucleotides. The plasmid strands were separated by alkaline denaturation (1 M NaOH, 1 mM EDTA; 5 min.) prior to the reaction. The entire cDNA was sequenced from both strands and all sequences were confirmed by unidirectional sequencing of a second overlapping clone. Internal EcoRI sites were verified by sequencing parts of the clones in lambda DNA according to the method of Manfioletti and Schneider, Nucleic Acid Res. 16:2873-2884 (1988), which is incorporated herein by reference. For this purpose, 10μg lambda DNA was heat denatured prior to reaction. Annealing of specific primers (50ng) was done for 5 minutes at room temperature.

Sequence analysis and databank comparisons

Editing and analysis of the sequence was done using MicroGenie (Beckman) and PCGene (Intelligenetics) software. Sequence comparisons with the databases Genbank (release 58.0), EMBL (17.0), NBRF/PIR (18.0) and SWISS-PROT (9.0) were performed on Bionet (Intelligenetics) using the Pearson-Lipman-algorithm (Pearson and Lipman, 1988) with ktup values of 4 and 1 for DNA- and protein-analysis, respectively.

EXAMPLE II

Expression of versican and versican NH2-terminal domain from cDNA

Figure 3:
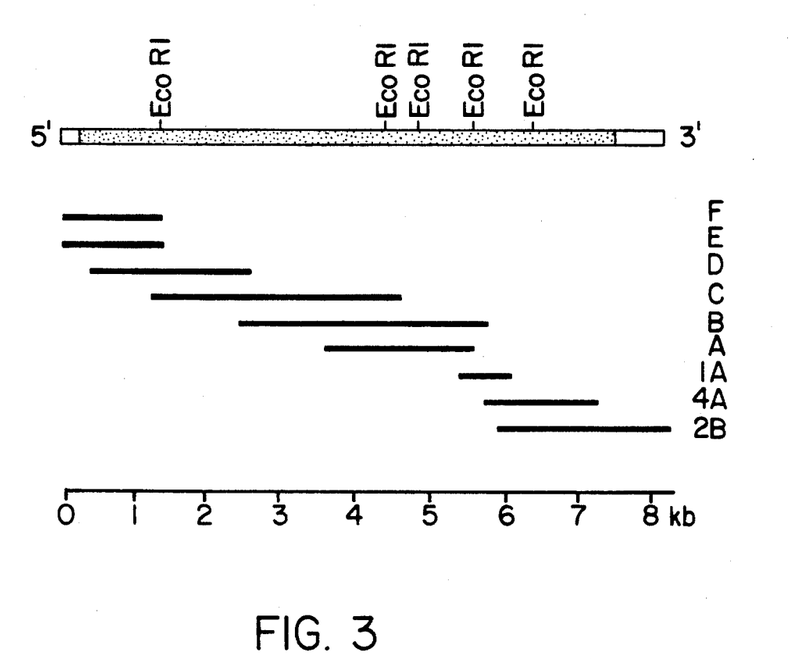
FIG. 3 shows the localization and nomenclature of the overlapping cDNA clones coding for versican.

The full-length versican cDNA and the versican NH2-terminal domain cDNA are assembled following procedures well known in the art. Each cDNA starts at the 5' untranslated region of the cDNA clone described in Zimmerman and Ruoslahti (*EMBOJ.*, 8:2975-2981 (1989)) which is incorporated herein by reference. As described in this reference, screening of a placental library resulted in the isolation of six overlapping cDNA clones that cover the entire coding sequence of versican (7227 bp) as well as 266 bp of 5' and 731 bp of 3' flanking sequence shown in FIG. 1. The six overlapping cDNA clones are shown in FIG. 3. To prepare and screen the cDNA library, a λgt11 expression library was prepared using poly(A)+ mRNA from cultured human IMR-90 fibroblasts as described in Krusius et al., *Proc. Natl. Acad. Sci. (USA)* 83:7683-7687 (1986). This library was screened using the proteoglycan antiserum diluted 1:100 or affinity-purified antibodies diluted to 1 μg/ml. Peroxidase-labeled goat anti-rabbit IgG second antibody (Bio-Rad) was used to visualize positive plaques.

cDNA inserts were isolated by preparative electrophoresis and used to construct M13 deletion libraries. Overlapping clones from such libraries were sequenced by the dideoxynucleotide chain termination method using the M13 universal primer oligonucleotide (Bethesda Research Laboratories) or oligonucleotides prepared for the cDNA sequence as primers in Krusius et al. (1986), supra. In the NH2-terminal domain cDNA, a stop codon is placed around nucleotide residue 1700 (FIG. 1), whereas the full-length clone includes all of the coding sequence shown in FIG. 1.

For expression, the cDNAs are inserted into the mammalian expression vector pSV2 (Mulligan and Berg, *Science* 209:1423 (1980)) which is incorporated herein by reference. Mulligan and Berg, supra describe the subcloning operations used to obtain Ecogpt and its subsequent insertion into various pSV expression vectors, including pSV2. Briefly, the DNA used for the isolation of the Ecogpt gene was a λ phage containing an insertion of 6 kbp of *E. coli* DNA spanning the pro gpt lac region of the *E. coli* chromosome. This phage, λgpt, efficiently transduces a variety of Gpt strains, including pro gpt lac deletion strains, to Gpt+. λgpt DNA was sheared to an average size of 2 kbp and short dT (deoxythymidylate) chains were added to the termini of the sheared fragments. The poly(dT) tailed phage DNA was annealed with poly(dA) tailed Eco RI endonuclease-cleaved pMB9 DNA. Then the recombinant molecules were transfected into *E. coli* JW2, a Gpt− purE strain (the purE mutation prevents de novo synthesis of purine nucleotides). Tetracycline-resistant (tet') clones were screened for Gpt+ colonies by their ability to grow on a minimal salts medium (M9) containing clucose, vitamin-free casamino acids, thiamine, tryptophan, and 60 μg of guanine per milliliter. Plasmid DNA isolated from one such colony was found by restriction endonuclease analysis to contain a 1.6-kbp segment of *E. coli* DNA. Transfection of JW2 and *E. coli* GP120—a Gpt− deletion strain—with this plasmid DNA (pPt-1) yielded tet' transformants that were all Gpt+. Recombinant plasmids containing the Ecogpt segment in the opposite orientation were also obtained and these transformants were also Gpt+. The SGPRT activity in extracts from Gpt− or wold-type strains carrying pPt-1 DNA was 20-fold higher than that found in wild-type *E. coli* strains. To obtain a smaller segment encoding the Ecogpt gene, pPt-1 DNA was cleaved with Bgl I and Hind II endonucleases, and the 1-kbp fragment from within the Ecogpt insert was isolated by gel electrophoresis. The Bgl I endonuclease generated end of this fragment was made blunt by treatment with *E. coli* DNA polymerase and the four deoxyribonucleoside triphosphates. A mixture of decanucleotide linkers containing Hind III and Bam HI endonuclease recognition sequences (Collaborative Research) (each in 40-fold molar excess) were ligated to the blunt ends of the Ecogpt fragment with T4 DNA ligase. After restriction endonuclease digestion with both Bam HI and Hind III endonucleases, the fragment was ligated to Hind III and Bam HI cleaved pBR322 DNA with T4 DNA ligase. After restriction endonuclease digestion with both Bam HI and Hind III endonucleases, the fragment was ligated to Hind III and Bam HI cleaved pBR322 DNA with T4 DNA ligase. Transfection of the Gpt− strain of *E. coli* with the hybrid DNA molecules yielded Gpt+ clones that contained both orientational isomers of the Ecogpt insert.

Dihydrofolate reductase (dhfr)-negative CHO are then cotransfected by the calcium phosphate coprecipitation method and cultured. Colonies arising from transfected cells are picked using cloning cylinders, expanded and checked for the expression of versican by immunoprecipitation. Clones expressing a substantial amount of versican can then be subjected to gene amplication by stepwise increasing concentration of methotrexate (MTX) as described in Kaufman and Sharp, *J. Mol. Biol.* 159:601 (1982), which is incorporated herein by reference.

In Kaufman and Sharp, a modular DHFR gene was constructed. The recombinant clones used to construct the DHFR gene were: (1) the Ad2 (adenovirus 2) major late promoter clone containing approximately 900 basepairs of adenovirus from 14.5 to 17.0 map units cloned into pBR322 between the HindIII and BamH1 sites: (2) a 3' splice site junction clones from an immunoglobulin variable region gene; and (3) a DHFR cDNA clone (pDHFR26). In order to reconstruct tetracycline resistance in the Ad2 major late promoter clone, the cloned DNA was digested with BamH1 and treated with $S_1$ nuclease ($10^2$ units/10 μl) at 10° C. for 30 min. After extraction with phenol, extraction with ether, and precipitation with ethanol, EcoRI linkers (Collaborative) were added with DNA T4 ligase. After heating to 65° C. for 15 min, the DNA digested with an excess of EcoRI restriction endonuclease and electrophoresed on a low melt agarose (BRL) gel. The 900 base-pair band was eluted and cloned into the EcoRI site of pBR322.

DNA from a clone containing 145 to 17 map units of adenovirus 2 in the EcoRI site was digested to completion with Pst1 and partially digested with HindIII. A 45kb band was isolated from a low melt agarose gel and ligated to the 90 base-pair PstI/HindIII fragment isolated from clone 6 (Bothwell et al., 1981) by electrophoresis on an acrylamide gel. Clones were isolated and shown to contain Pst1, HindIII, and BglII sites representative of the 90 base-pair insert. This DNA was digested with PstI and ligated to the 1375 base-pair insert isolated from pDHFR26 by digestion with Pst, electrophoresis, and extraction from a low melt agarose gel. After transformation of competent *Escherichia coli* C600, colonies appearing on tetracycline plates were screened by filter hybridization to the nick-translated DHFRcDNA insert. Positively hybridizing clones were tested by restriction endonuclease digestion. Two clones pAdD26-1 and pAdD26-2 which contained the cDNA in correct orientation with the adenovirus major late promoter (pAdO26-1) and which contained the DHRF cDNA in the opposite orientation of the DHFR cDNA (pAdD26-2) were prepared by twice banding to equilibrium in CsCl/ethidium bromide gradients.

SV40 (strain 776) was cloned into the pAdD26 clones described above by ligation to the EcoRI site. DNA from the pAdD26 clones were digested with EcoRI, treated with calf intestine phosphatase, and extracted with phenol, ether, and precipitated with ethanol. EcoRI-cut SV40 DNA was ligated to each plasmid DNA and these reactions were used to transform *E. coli* C600 to tetracycline resistance. Clones were screened by restriction endonuclease sensitivity and DNA from 4 clones pASD112, pASD12, pASD21, and pASD22 was prepared in large amounts by banding twice in CsCl/ethidium bromide gradients. pASD11 and pASD21 contain SV40 late transcription in the same direction as the adenovirus late promoter, and pASD12 and pASD22 contain SV40 early transcription in the same direction as the adenovirus late promoter, pASD11 and pASD12 have the DHFR cDNA in the correct orientation with the adenovirus late promoter, and plasmids pASD21 and pASD22 have the DHFR cDNA in the opposite orientation as the adenovirus late promoter.

For restriction endonuclease digestion of genomic CNA and blot hybridization, high molecular weight cellular DNA was first isolated. A total of 11 μg of genomic CNA was digested with the indicated restriction endonuclease (New England Biolabs) and completion was monitored by incubation of a portion of the reaction (containing 1 μg DNA) with 0.5 μg of bacteriophase λ DNA which was analyzed by agarose gel electrophoresis. Reactions were stopped by adding EDTA to 10 mM, glycerol to 5%, and bromphenol blue. Samples were electrophoresed on 1.1% (w/v) agarose gels in E' buffer (50 mM-Tris, pH 8.3, 50 mM-sodium acetate, 6 mM-EDTA). The gel was strained in 5 μg ethidium bromide/ml and irradiated 5 min under a short wavelength untraviolet lamp in order to insure good transfer of large fragments from the gel. Following denaturation and subsequent neutralization, the DNA was transferred from the gel to nitrocellulose filter paper (Millipore) according to Southern with minor modifications. The filters were then marked to indicate positions of HindIII-digested λ DNA molecular weight markers, rinsed in 2×SSC (SSC is 0.15 M-NaCl, 15 mM-sodium citrate) and baked in vacuo for 2 h at 80° C.

For hybridization, filters were pretreated longer than 4 h in 50% (v/v) formamide, 3×SSC (pH 7.4), 0.5% sodium dodecyl sulfate, 1×Denhardt's reagent at 42° C. Hybridizations were carried out in prehybridization solution (15 ml) with addition of 10% (w/v) dextrate sulfate. 20 μg denatured salmon sperm DNA;/ml, and $5 \times 10^6$ cts/min of denatured specific DNA probes which were prepared by nick-translation using [s-$^{32}$P]dCTP and [X-$^{32}$]dATP (450 Ci/mmol) and had $^{32}$P-specific activities greater than $2 \times 10^8$ μg.

Hybridizations were allowed to proceed 8 to 16 h at 42° C. Filters were than washed twice in 5×SSC with 0.5% sodium dodecyl sulfate at 68°%, and twice in 2×SSC at room temperature. Filters were air-dried and prepared for autoradiography using preflash Kodak XR-5 film with Dupont lighting-plus intensifying screens at −70° C. Nitrocellulose filters re-used for hybridizations were washed in 0.1 M-NaOH, 2×SSC at room temperature for 20 min. rinsed twice in 2×SSC and then pretreated for hybridization. Copy numbers of amplified DNA were determined by comparing hybridization to the 1 kb band generated by BamH1 digestion in clones 1B and 1D to intensities from the same fragment from reconstructions using increasing amounts of plasmid pASD11 in the presence of CHO DNA.

Ten clones were isolated from cells transfected with either pASD11 or pASD12 and DNA prepared for Southern blot analysis. BamH1-digested genomic DNA was analyzed after gel electrophoresis and southern transfer for hybridization to either radioactively labeled pDHFR26 or pBR322. All clones were found to contain transforming DNA integrated into one to five sites in cellular DNA. Three clones from pASD11 (1B, 1C, and 1D) and one from pASD12 (2B) transformed cells were chosen for subjection to stepwise MTX selection. Sequential growth in 0.01, 0.02, 0.1 and 1 μM-methotrexate yielded cell lines which were than analyzed by Southern blot analysis. All clones have dramatically amplified the transforming DNA in the selection process. In particular, clone 1C shows an approximately 100-fold amplification of the band originally present. Clone 1D has preferentially amplified the highest molecular weight segment of the several bands initially present (obviously from a lighter exposure). Clones 1B and 2B have rearranged the transforming DNA in the amplification process.

Although the invention has been described with reference tot he presently-preferred embodiment, it should be understood that various modifications can be made without departing from the spirit of the invention. Accordingly, the invention is limited only by the following claims.

We claim:

1. As a product of recombinant DNA, isolated and purified versican core protein having substantially the amino acid sequence of FIG. 1 and exhibiting binding activity to hyaluronic acid.

2. An isolated nucleic acid sequence which encodes versican core protein, said sequence having substantially the nucleic acid sequence of FIG. 1.

3. The nucleic acid sequence of claim 2, where said sequence is cDNA.

4. The nucleic acid sequence of claim 2, wherein said nucleic acid sequence is transcribed into mRNA.

5. Isolated antibodies that bind to versican core protein.

6. The antibodies of claim 5, wherein the antibodies are polyclonal.

7. The antibodies of claim 5, wherein the antibodies are monoclonal.

* * * * *

UNITED STATES PATENT AND TRADEMARK OFFICE
CERTIFICATE OF CORRECTION

PATENT NO. : 5,180,808
DATED : January 19, 1993
INVENTOR(S) : Erkki I. Ruoslahti It is certified that error appears in the above-identified patent and that said Letters Patent is hereby corrected as shown below:

In column 1, line 7, insert new paragraph:

--This invention was made with government support under Grant Numbers CA28896 and CA42507 awarded by the National Institutes of Health. The government has certain rights in the invention.--.

In column 1, line 18, after "vary in size from" change "1,000" to --11,000--.

In column 1, line 47, after "acid and" change "Nacetylglucosamine" to --N-acetylglucosamine--.

In column 3, line 19, after "$Ala_{20}$ and" change "$Leu_2$," to --$Leu_{21}$,--.

In column 3, line 63, after "additional" change "serineglycine" to --serine-glycine--.

In column 7, line 30, after "The" change "SGPRT" to --XGPRT--.

In column 7, line 31, after "or" change "wold-type" to --wild-type--.

In column 8, line 49, after "clones" change "pASD112," to --pASD11,--.

In column 8, line 61, change "CNA" to --DNA--.

In column 8, line 63, change "CNA" to --DNA--.

In column 9, line 17, after "formamide," change "3 x SSC" to --5 x SSC--.

UNITED STATES PATENT AND TRADEMARK OFFICE
CERTIFICATE OF CORRECTION

PATENT NO. : 5,180,808
DATED : January 19, 1993
INVENTOR(S) : Krkki I. Ruoslahti It is certified that error appears in the above-identified patent and that said Letters Patent is hereby corrected as shown below:

In column 9, line 23, after "using" change "[s-" to --[x- --.

Signed and Sealed this

Seventeenth Day of May, 1994

BRUCE LEHMAN

*Attest:*

*Attesting Officer*     *Commissioner of Patents and Trademarks*